United States Patent [19]
Lemelson

[11] Patent Number: 5,525,240
[45] Date of Patent: Jun. 11, 1996

[54] ADAPTIVELY CONTROLLED CENTRIFUGATION METHOD

[76] Inventor: Jerome H. Lemelson, Suite 286, Unit 802 930 Tahoe Blvd., Incline Village, Nev. 89451-9436

[21] Appl. No.: 174,183

[22] Filed: Dec. 27, 1993

[51] Int. Cl.$^6$ .................. G01N 15/06; B01D 21/26
[52] U.S. Cl. .................. 210/745; 210/739; 210/787; 210/789; 73/61.71; 356/318; 422/72; 422/82.08; 436/45; 436/172
[58] Field of Search .................. 210/94, 96.1, 739, 210/745, 787, 789; 73/61.71; 422/72, 82.08; 436/45, 172; 356/318

[56] References Cited

U.S. PATENT DOCUMENTS

| | | | |
|---|---|---|---|
| 4,421,860 | 12/1983 | Elings et al. | 356/318 |
| 5,055,202 | 10/1991 | Carroll et al. | 210/739 |
| 5,308,506 | 5/1994 | McEwen et al. | 210/745 |

*Primary Examiner*—Robert A. Dawson
*Assistant Examiner*—David A. Reifsnyder
*Attorney, Agent, or Firm*—J. Kevin Parker

[57] ABSTRACT

An apparatus and method are disclosed in which the centrifugation of a liquid mixture in order to separate out components of the mixture with different sedimentation rates is adaptively controlled by monitoring the sedimentation of detectable particles and controlling the centrifugation so as to effect a desired localization of the detectable particles. Such adaptive control may be performed with a continuous flow centrifugal separator or a batch-type centrifuge. The detectable particles may be test particles having a sedimentation constant approximately equal to a component of interest in the mixture whose localization is desired.

10 Claims, 3 Drawing Sheets

1 …

ADAPTIVELY CONTROLLED CENTRIFUGATION METHOD

BACKGROUND AND SUMMARY OF THE INVENTION

A common method for separating out heavier components from a liquid mixture is the use of centrifugation, whereby the mixture is subjected to a centrifugal force field which causes the sedimentation of the components at different rates according to their densities and volumes. In a centrifuge for separating biological cells, for example, a suspension of cells in a liquid medium is placed in a centrifuge tube which is rotated rapidly about an axis some distance from the tube so as to cause sedimentation of the cells and other structures toward the bottom of the tube. Cells or other particles may thus be separated differentially by varying the time of centrifugation with the denser components sealing at the bottom of the tube first. Such differential centrifugation is commonly used, for example, to separate red blood cells from white blood cells owing to the greater density of the former. After disruption of cells into a heterogeneous liquid, centrifugation is also used to separate cellular constituent parts such as nuclei, mitochondria, ribosomes, etc.

Any heterogeneous liquid mixture may be subjected to centrifugation. A more clearly demarcated degree of separation may be achieved, however, by interposing a density barrier which only particles having a greater density may penetrate. For example, a blood cell suspension may be layered over a solution of albumin or sucrose whose density is between that of red and white cells, allowing the red cells but not the white cells to go through the density barrier which affords a better separation. Modifications of this technique, called density gradient centrifugation, include using a centrifuge medium having a number of layers of varying density or using a medium having a continuous density gradient along the length of the centrifuge tube. If the different densities of the medium encompass the range of densities represented by the different components desired to be separated, each component will come to rest in a layer of the medium whose density matches its own.

Centrifugation may also be used in a continuous flow process in which heavier or lighter components are removed from a feedstock. Centrifugal separators of this type are commonly used in the dairy and paper industries as well as in isotopic separation processes. Since the liquid which is centrifuged in these cases is the feedstock itself and not a special centrifugation medium, it is usually not possible to employ the density gradient technique as described above to enhance the degree of separation of the components. A cleaner separation may be achieved, however, by the use of multi-stage centrifugal separators in which the feedstock is continuously depleted of either the heavier or lighter components as it proceeds through the multiple stages.

In any of the centrifugal separation processes described above, it would be advantageous if the centrifuge could be operated so as to optimize the separation of a select component or components from the rest of the mixture. For example, in density gradient centrifugation, the centrifugation must proceed long enough for the different particles to localize in their individual density layers. How long this takes depends on the sedimentation constants of the particles, the rotational speed of the centrifuge, and the composition of the centrifuge medium. If the centrifugation is allowed to proceed for too long and at too high a speed, however, disruption of the desired layers as well as fragile components such as cells may occur. In accordance with the present invention, therefore, a quantity of detectable test particles having a sedimentation constant approximately equal to that of a select component of a mixture which it is desired to separate is added to the mixture before or during the centrifugation. Such test particles, depending upon the type of mixture component whose sedimentation rate they are designed to emulate, may be either molecules or larger particles to which is conjugated a tag enabling the test particle to be detected by electro-optical or other means. The position mid/or velocity of the test particles in the mixture as centrifugation proceeds is monitored by a scanning device which feeds the position data to a computer which then controls the speed and duration of the centrifuge so as to result in a desired localization of the component which it is desired to separate. By means of such adaptive control of the centrifuge, its operation may be optimized to separate out a select component even as the composition of the centrifuge medium varies. The technique is thus especially useful in those applications where centrifugation takes place in a native medium subject to a great deal of variability as opposed to an artificial centrifuge medium.

The present invention may also be used in continuous centrifugal separation operations to control the speed of each of the individual centrifugal separation stages so as to result in the optimum separation of a select component or components from the feedstock. Other variables which may also be controlled include impeller blade angles and rate of throughput into each stage. In a continuous separation operation, test particles are continuously added to the feedstock, and the concentration of the particles is continuously monitored in the product coming out of the separator. A plurality of different test particles may also be used with each having a sedimentation constant corresponding to a different component of the feedstock. Select components may then be optimally stripped from the feedstock by removing product frown select stages and operating the stages in accordance with the concentration of test particles in each product stream. In cases where it is desired to remove the test particles from the product, the particles may be composed or partly composed of a ligand having a binding affinity for specific molecules immobilized in a reaction column. The test particles may then be separated from the rest of the product by passing the product through the reaction column.

It is a primary object of the invention to employ a computer and electro-optical or radiation scanning devices in order to adaptively control the operation of a centrifugal separator.

It is a further object of the invention to operate a centrifuge in an adaptive manner which optimizes the separation of a select component from a heterogeneous mixture.

It is a further object of the invention to operate a centrifuge so as to localize a select component of a heterogeneous mixture in a centrifuge medium of varying density.

Other objects, features, and advantages of the invention will become evident in light of the following detailed description considered in conjunction with the referenced drawings of a preferred exemplary embodiment according to the present invention.

DETAILED DESCRIPTION OF THE INVENTION

Figure 1:
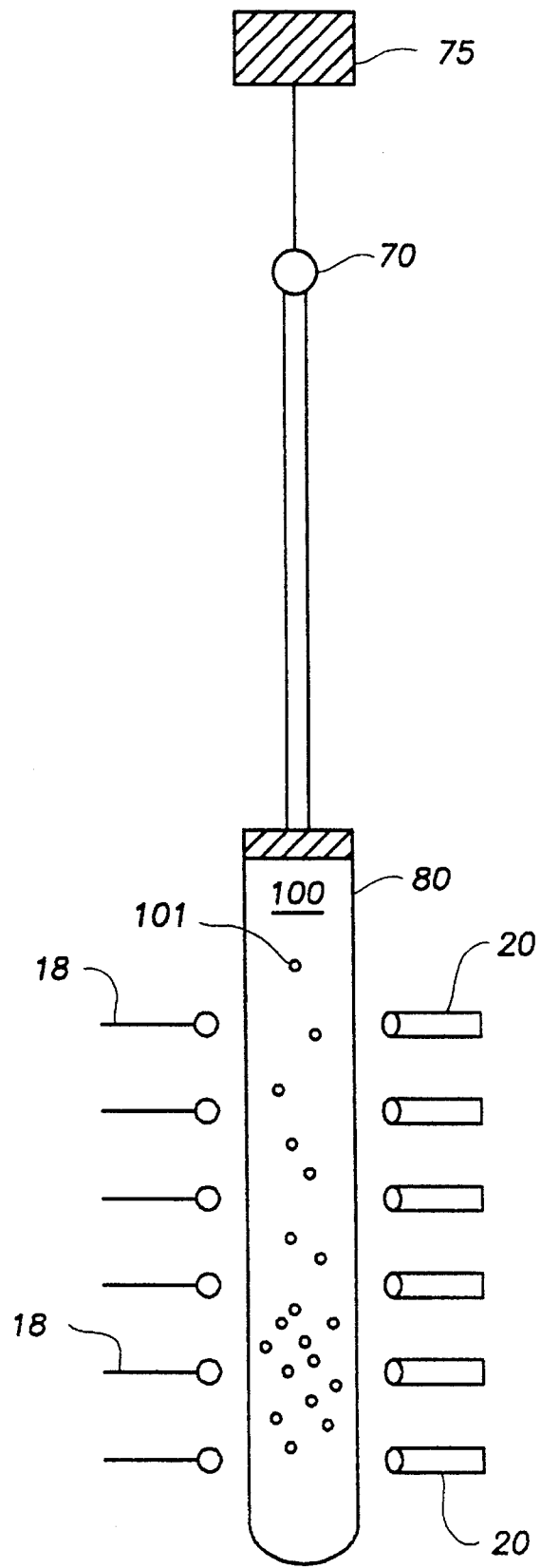
FIG. 1 shows a laboratory type centrifuge for separating components into layers within the centrifuge tube.

FIG. 1 illustrates the present invention as applied to a typical centrifuge for separating biological components, such as cells or organelles, in a heterogeneous mixture. The centrifuge comprises a centrifuge tube 80 which is rotated with a counterweight 5 about an axis defined by a rotor 70 which is driven by conventional mechanical drive means. The mixture 100 is contained in centrifuge tube 80 and may or may not include an additional medium for setting up density gradients within the tube. Mounted in fixed relation to the tube 80 so as to rotate along therewith is an array of lasers 20 and photodetectors 18 for monitoring the presence of test particles 101 within the mixture. Test particles 101 may consist of molecules or particles conjugated to molecules having specific spectral absorption or scattering characteristics so as to give a spectral signature detectable by photodetectors 18. One type of molecule which may be conjugated to the test particle is a fluorescent label such as fluorescein or rhodamine which are commonly used in flow cytometry. The test particles are then detected by means of a laser L for exciting the fluorescent dye molecules and a photodetector P for measuring the light scattered and/or emitted by the fluorescent molecules. The laser is operated in a scanning fashion so that the beam intersects with a large portion of the fluid passing by. The signal produced by the photodetector P varies in accordance with the quantity of test particles present in the mixture and is fed to computer 11.

Figure 3:
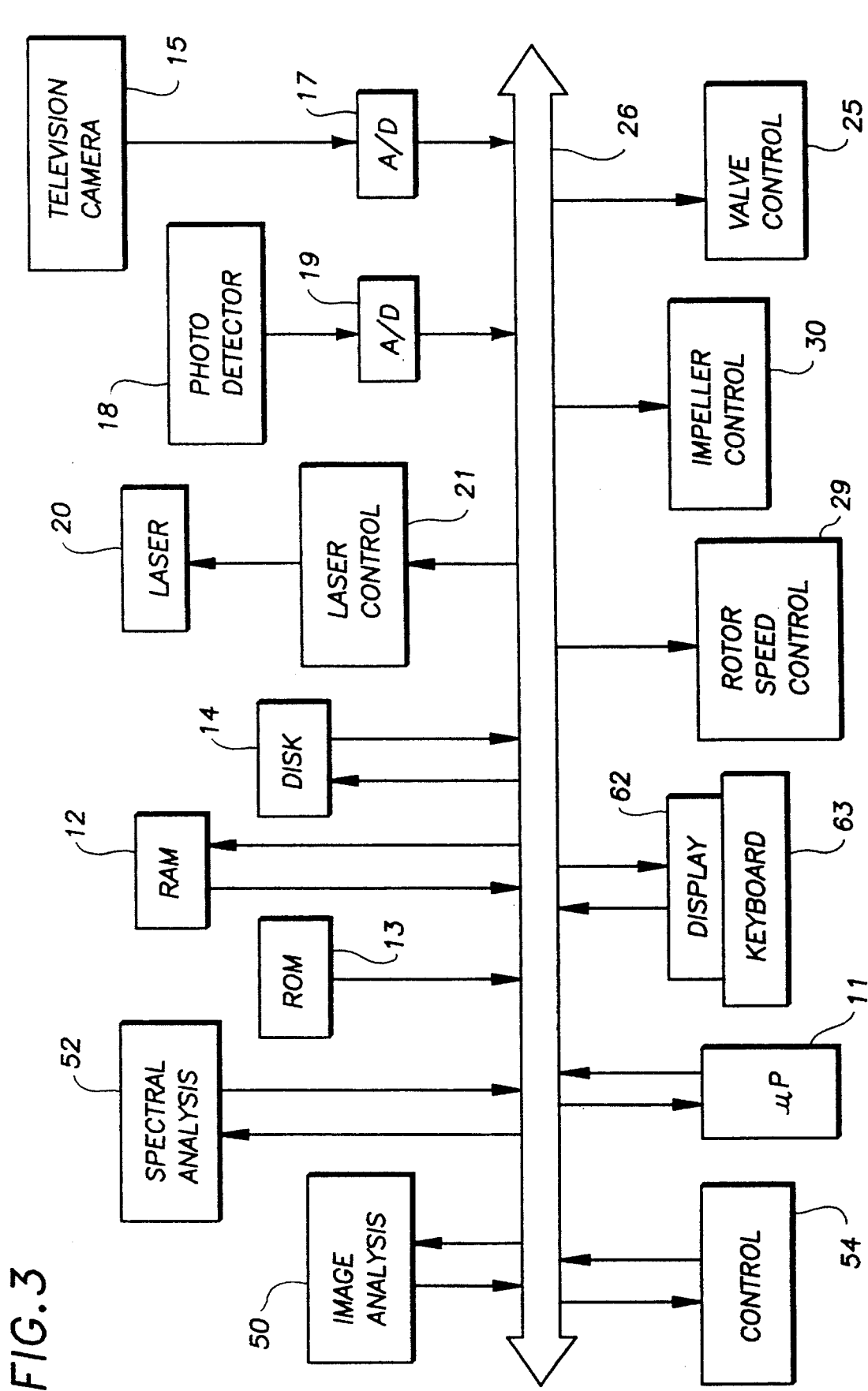
FIG. 3 shows an exemplary computer system for controlling the operation of a centrifugal separator.

The centrifuge in FIG. 1 is controlled in its operation by a computer 11 as shown in FIG. 3 at a speed and for a duration which results in the localization of the test particles 101 in a desired sedimentation layer of tube 80. To accomplish this, the computer is supplied with the data generated by phototdetectors 18 which places the location of the test particles 101 in the tube 80. The test particles 101 are chosen so as to have a sedimentation constant approximately equal to the actual mixture component of interest which it is desired to localize at a given layer. The component of interest may consist of large particulate components, such as whole cells, or particular molecules. The location of the test particles thus corresponds to the location of the component of interest. In some applications, the component of interest may consist of detectable particles allowing for direct localization without the need of test particles.

Figure 2:
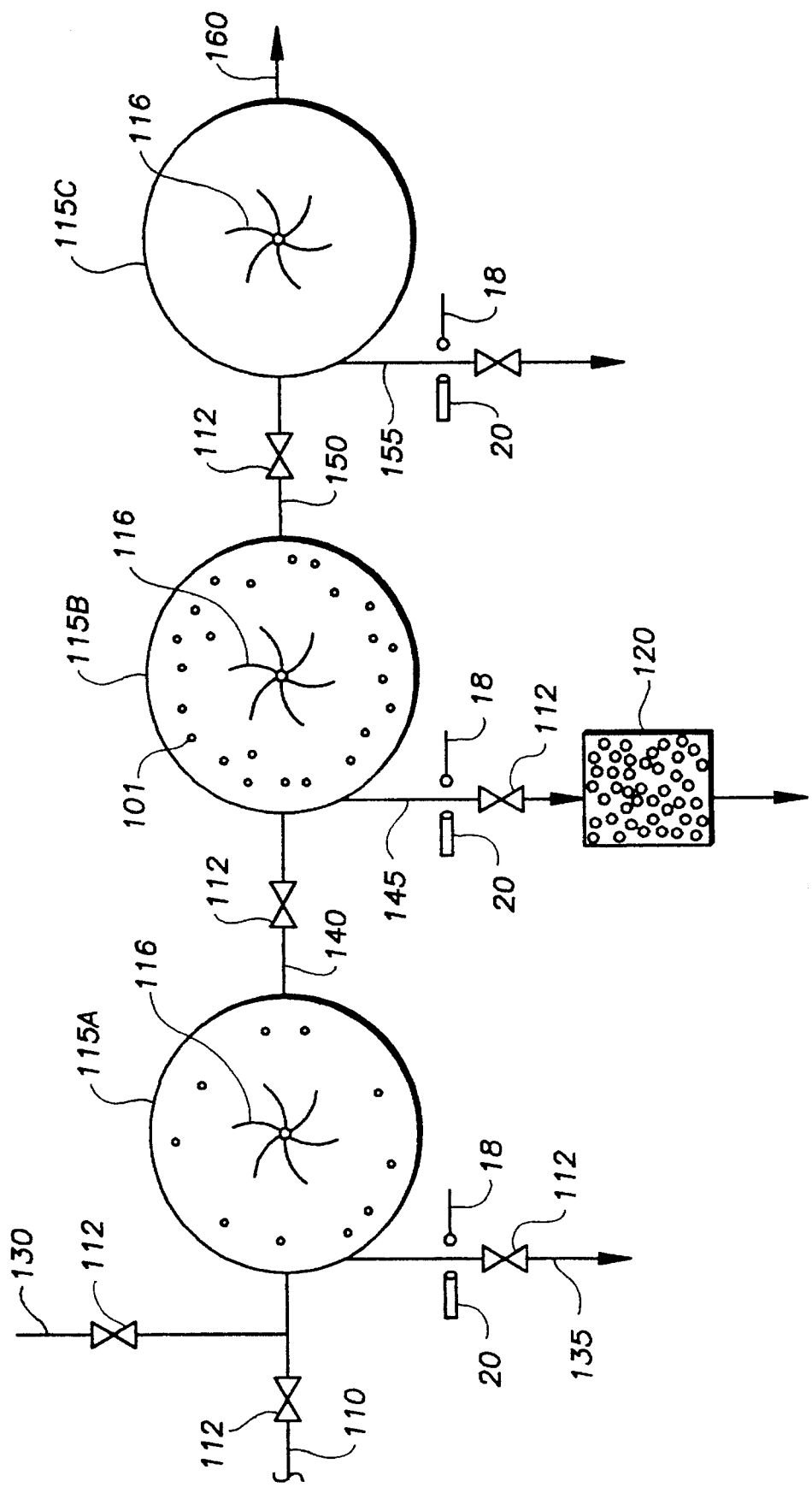
FIG. 2 shows an exemplary multi-stage centrifugal separator for stripping dense components from a feedstock stream.

An exemplary multi-stage centrifugal separator is illustrated schematically in FIG. 2 which includes stages 115A through 115C through which a feedstock fluid flows. The feedstock fluid flows initially as stream 110 into the housing of centrifuge stage 115A where it is made to rotate by impeller 116. The denser components of the feedstock fluid sediment faster than lighter components toward the periphery of the housing and accumulate there. A stripping stream 135 removes these dense components from the feedstock which then flows consecutively to stages 115B and 115C (designated as streams 140 and 150, respectively) which operate similarly so that components of next higher density are removed by stripping streams 145 and 155, respectively. The feedstock emerging as product in line 160 has thus been progressively stripped of dense and rapidly sedimenting components. The most dense components come off in the first stage, the next densest in the next stage, and so on. The exact density of the fluid in each of the streams 135, 145, and 155 for a given feedstock, however, depends on a number of variables including the speed of the impellers and the rate at which fluid flows between and out of the stages. By controlling these variables in accordance with appropriate feedback signals, the separator may be operated so as to maximize (or minimize) the quantity of fluid components having a particular density in a particular stream. To provide the feedback signals, test particles are injected into the feedstock by stream 130, and their concentrations in streams 135, 145, and 155 are monitored using lasers 20 and photodetectors 18. Test particles may also be used which are detectable by other means such as optical scanning of the fluid to form images and scintillation counting of radiation emitted by radioactively labeled test particles. By whatever means the test particles are detected, the resulting data signals from the test particle sensors are fed to a computer which then adjusts valves 112 controlling the flows in the various streams and the impeller speeds of the stages in a manner so as to result in the desired concentration of test particles in a particular stream. As described above, the test particles are designed to have the same sedimentation constant as the component of interest so that the latter's concentration is necessarily also controlled. A plurality of different types of test particles may also be employed to control the concentrations of a plurality of components.

In certain applications of the invention, the component of interest may itself be detectable so as to obviate the need for test particles. For example, if centrifugal separation is used to remove radioactive particles from water, the concentration of radioactive particles in a particular stream may be directly monitored with a scintillation counter. Other components of interest may be directly detectable by other means.

If the separator is operated so that a particular component of interest is maximized in a product, the product necessarily contains a high concentration of test particles. It may be desireable to remove these test particles from the product. Such removal of the test particles cannot by accomplished by differential sedimentation or filtering without also removing the component of interest, however, due to their deliberately similar size and density. The test particles may therefore also include a ligand having a binding affinity for a specific molecules immobilized in a reaction column. Such a reaction column 120 is shown in FIG. 2 as removing the test particles from stream 145. Examples of molecular binding pairs which may be employed include complementary nucleic acid sequences, avidin/biotin, and lectins/carbohydrates, with one member of the pair being immobilized within the reaction column and the other conjugated to the test particle.

FIG. 3 shows an exemplary system for controlling the operation of a centrifugal separator such as illustrated in FIG. 2 in accordance with the present invention. A microprocessor or computer 11 controls the test particle detection and control actions by receiving and gating digital detection and control signals to and from various electrically operated devices and subsystems. The microprocessor 11 is shown as connected via bidirectional data bus 26 to various peripheral components including RAM 12, ROM 13, disk storage device 14, keyboard 63, display 62, as well as other components as described below. Scanning a fluid to detect test particles is effected by one or more imaging devices and/or spectral radiation detection devices such as photoelectric detector 18 which may be used alone or with a plurality thereof and one or more attendant lasers 20 to scan across a duct such as a pipe through which a mixture whose components are to be separated is flowing. The output of detector 18 is a variable electrical signal which is digitized by an analog-to-digital converter 19 and passed to data bus 26 for analysis by a spectral radiation analysis module 52. Similarly, the output of a television camera 15 is passed via analog-to-digital converter 17 to the system for analysis by image analysis module 50. In a preferred embodiment, the computed digital code signals output by either or both the image analyzing and spectral radiation signal analyzing modules 50 and 52 are applied by microprocessor 11 to a control module 54 for analysis using expert systems, fuzzy logic and/or neural network techniques, where the aforementioned modules may be either dedicated hardware components or software programs. The output of the control module 54 is then used to optimize the operation the centrifugal separator by controlling the operation of various fluid flow control valves through a valve control 25, controlling the adjustment of the impellers for each centrifuge stage through impeller angle control 30, and the speed of each centrifuge stage through impeller speed control 29.

Although the invention has been described in conjunction with the foregoing specific embodiments, many alternatives, variations, and modifications will be apparent to those of ordinary skill in the art. Those alternatives, variations, and modifications are intended to fall within the scope of the following appended claims.

What is claimed is:

1. A method for separating components of a liquid mixture wherein said liquid mixture is a continuously flowing feedstock comprising the steps of:

imparting rotation to a housing containing said liquid mixture about an axis of the housing so as to cause the sedimentation of denser components radially outward from the axis of rotation;

removing denser sedimented components of the liquid mixture in a stripping stream and leaving residual components in an output stream;

injecting specific test particles into the liquid mixture;

scanning said liquid mixture with a scanning device for the presence of said specific test particles injected into the liquid mixture and generating signals relating thereto; and computer controlling with control signals the rotation of said liquid mixture so as to effect a desired concentration of specific particles in a particular stream as indicated by said scanning signals.

2. A method in accordance with claim 1 wherein said desired localization results in the formation of a particular sedimentation layer in a centrifuge tube containing said liquid mixture.

3. A method in accordance with claim 1 further comprising the step of disposing test particles detectable by said scanning device into said liquid mixture, wherein the localization of said test particles is effected by said computer and further wherein said test particles have a sedimentation constant approximately equal to a component of interest in the liquid mixture.

4. A method in accordance with claim 1 further comprising the step of injecting test particles detectable by said scanning device into said feedstock, wherein the localization of said test particles is effected by said computer and further wherein said test particles have a sedimentation constant different from a component of interest in the feedstock.

5. A method in accordance with claim 4 further comprising the step of flowing a particular stream into a reactor column, said reactor column containing immobilized molecules for removing said test particles by binding therewith.

6. A method in accordance with claim 4 wherein said scanning step is performed by a laser for irradiating said test particles in the mixture with light and a photodetector for detecting the light scattered thereby.

7. A method in accordance with claim 4 wherein said test particles are fluorescently labeled and further wherein said scanning step is performed by a laser for irradiating said test particles in the mixture with light and a photodetector for detecting the light scattered or emitted thereby.

8. A method in accordance with claim 4 wherein scanning is effected by photoelectrically detecting fluorescent radiation generated by directing laser radiation at said test particles in said liquid.

9. A method in accordance with claim 4 further comprising the step of controlling the flowrate of a particular stream with a control valve actuated by said computer in a manner so as to effect a desired concentration of specific particles in a particular stream.

10. A method in accordance with claim 1 wherein said test particles emit fluorescent radiation when irradiated and further wherein scanning is effected by photoelectrically detecting fluorescent radiation generated by directing laser radiation at select particles in said liquid.

* * * * *